(12) United States Patent
Koehler et al.

(10) Patent No.: US 11,759,159 B2
(45) Date of Patent: Sep. 19, 2023

(54) APPARATUS FOR GENERATING X-RAY IMAGING DATA

(71) Applicant: KONINKLIJKE PHILIPS N.V., Eindhoven (NL)

(72) Inventors: Thomas Koehler, Hanorderstedt (DE); Gereon Vogtmeier, Aachen (DE); Andriy Yaroshenko, Kiryat Bailik (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/263,570

(22) PCT Filed: Aug. 1, 2019

(86) PCT No.: PCT/EP2019/070747
§ 371 (c)(1),
(2) Date: Jan. 27, 2021

(87) PCT Pub. No.: WO2020/025741
PCT Pub. Date: Feb. 6, 2020

(65) Prior Publication Data
US 2021/0298704 A1   Sep. 30, 2021

(30) Foreign Application Priority Data

Aug. 1, 2018 (EP) .................... 18186798

(51) Int. Cl.
*A61B 6/00* (2006.01)
*A61B 6/03* (2006.01)

(52) U.S. Cl.
CPC ............. *A61B 6/484* (2013.01); *A61B 6/032* (2013.01); *A61B 6/4035* (2013.01); *A61B 6/4291* (2013.01)

(58) Field of Classification Search
CPC ....... A61B 6/484; A61B 6/032; A61B 6/4035; A61B 6/4291
See application file for complete search history.

(56) References Cited

U.S. PATENT DOCUMENTS

| | | | |
|---|---|---|---|
| 6,522,411 B1 | 2/2003 | Moon | |
| 7,639,786 B2 | 12/2009 | Baumann | |
| (Continued) | | | |

FOREIGN PATENT DOCUMENTS

| | | |
|---|---|---|
| DE | 102015201741 A1 | 8/2016 |
| DE | 102016200440 A1 | 7/2017 |
| (Continued) | | |

OTHER PUBLICATIONS

PCT International Search Report, International application No. PCT/EP2019/070747, dated Oct. 31, 2019.

*Primary Examiner* — Courtney D Thomas
(74) *Attorney, Agent, or Firm* — Larry Liberchuk

(57) ABSTRACT

The present invention relates to an apparatus (10) for generating X-ray imaging data. It is described to position (210) a first grating between an X-ray source and a second grating. The second grating is positioned (220) between the first grating and a third grating. A third grating is positioned (230) between the second grating and an X-ray detector. An object is positioned (240) between the first grating and the third grating. At least one of the three gratings has a pitch attribute of having a constant grating pitch. At least one of the three gratings has a pitch attribute of having a varying grating pitch. Both gratings of an adjacent pair of gratings are bent such that a distance between the two adjacent gratings is constant as a function of fan angle. Both gratings of the adjacent pair of gratings that are bent have the same pitch attribute. An X-ray detector detects (250) at least some of the X-rays transmitted by the three gratings and the object.

13 Claims, 3 Drawing Sheets

(56) References Cited

U.S. PATENT DOCUMENTS

| | | |
|---|---|---|
| 9,841,388 B2 | 12/2017 | Creux |
| 2013/0142307 A1 | 6/2013 | Nakamura |
| 2014/0226785 A1 | 8/2014 | Stutman |
| 2016/0135769 A1* | 5/2016 | Wang .................. A61B 6/484 378/36 |
| 2016/0290937 A1* | 10/2016 | Lu ...................... A61B 6/4035 |

FOREIGN PATENT DOCUMENTS

| | | |
|---|---|---|
| WO | WO2012029005 A1 | 3/2012 |
| WO | WO2015044238 A1 | 4/2015 |
| WO | WO2018046377 A1 | 3/2018 |

* cited by examiner

APPARATUS FOR GENERATING X-RAY IMAGING DATA

FIELD OF THE INVENTION

The present invention relates to an apparatus for generating X-ray imaging data, to a method for generating X-ray imaging data as well as to a computer program element and a computer readable medium.

BACKGROUND OF THE INVENTION

Differential phase-contrast and dark-field imaging (DPCI and DFI) are promising technologies that will likely enhance the diagnostic quality of X-ray equipment Computer Tomography (CT) and radiography systems. For example, Dark-field X-Ray (DAX) imaging is a new modality with a great potential in the area of diagnosing lung diseases like COPD, pulmonary fibrosis, lung cancer, etc. The basic concept for DAX imaging is to use a Talbot-Lau type interferometer, i.e., to add three gratings G0, G1, and G2 into the X-ray beam. The object can be placed either between the G0 and G1 gratings or between G1 and G2.

US2016/0135769A describes systems and methods for X-ray phase-contrast imaging (PCI). It is described that a quasi-periodic phase grating can be positioned between an object being imaged and a detector, and an analyzer grating can be disposed between the phase grating and the detector. Second-order approximation models for X-ray phase retrieval using paraxial Fresnel-Kirchhoff diffraction theory are also described. It is described that an iterative method can be used to reconstruct a phase-contrast image or a dark-field image.

One of the major challenges in the construction of a DAX system is the analyzer grating G2. It has to cover ideally the entire detector area (for example 43 cm×43 cm) and has to be highly attenuating (for example >90%). At the same time, the pitch is still demanding (in the ballpark of 15 to 40 μm period). Putting all these requirements together, it is clear that the grating lamellae must be focused to the source.

State of the art grating manufacturing is based on "Lithography, Electroplating and Molding" LIGA technology, which, however, has several limitations and shortcomings like the need to have access to a synchrotron or the need to work with grating tiles since the grating size is limited.

On the other hand, there is the mature technology of foil stacking that is currently established to produce anti-scatter grids. Most recent progress in this area indicates that it might be possible to reach the desired grating periods with this technology.

While the most recent progress in foil stacking might open the way for using this technology for G2, it is not feasible to use it for G0 (because the pitch is even smaller) and G1 (because this is a phase grating). Combining gratings manufactured by LIGA and foil stacking poses the problem of focusing. If gratings are manufactured using the LIGA process, the gratings are inherently flat and focused to infinity, i.e., all lamellae are parallel to each other. Focusing of the gratings is achieved by bending the substrates. However, on the other hand, gratings manufactured by foil stacking are flat and directly focused to a predefined distance. These gratings are very stiff and it is impossible to change the focus after manufacturing. In particular, it is impossible to manufacture a grating with a focus at infinity and bend it later on to the desired distance to the focal spot of the X-ray tube.

There is a need to address these issues.

SUMMARY OF THE INVENTION

It would be advantageous to have improved apparatus, method and system for phase-contrast and/or dark-field imaging.

The object of the present invention is solved with the subject matter of the independent claims, wherein further embodiments are incorporated in the dependent claims. It should be noted that the following described aspects and examples of the invention apply also to the apparatus for generating X-ray imaging data, the method for generating X-ray imaging data, as well as for the computer program element and a computer readable medium.

According to a first aspect, there is provided an apparatus for generating X-ray imaging data, comprising:
  an X-ray source;
  a first grating;
  a second grating;
  a third grating; and
  an X-ray detector.

The X-ray source is configured to produce X-rays. The first grating is positioned between the X-ray source and the second grating. The second grating is positioned between the first grating and the third grating. The third grating is positioned between the second grating and the X-ray detector. At least part of the region between the first grating and the third grating forms an examination region for accommodating an object. Either the first grating or the third grating has a pitch attribute of having a constant grating pitch. Both gratings of an adjacent pair of gratings have a pitch attribute of having a varying grating pitch. Both gratings of an adjacent pair of gratings are bent such that a distance between the two adjacent gratings is constant as a function of fan angle. The X-ray detector is configured to detect at least some of the X-rays transmitted by the three gratings.

In other words, G0, G1 and G2 gratings of a dark-field and/or phase-contrast arrangement are utilized, but with two of the gratings that are adjacent to each other being bent. Thus either G0 and G1 gratings are bent or G1 and G2 gratings are bent. Then either G0 and G1 gratings both have a varying grating pitch (chirped) and G2 has a constant pitch or G1 and G2 gratings have a varying pitch and G0 has a constant grating pitch. Thus, G0 and G1 can be bent and chirped and G2 have constant pitch and be planar, or G0 and G1 can be bent and G1 and G2 chirped with G0 having a constant pitch and G2 be planar, or G1 and G2 can be bent and G0 and G1 be chirped with G2 having a constant pitch and G0 can be planar or G1 and G2 can be bent and chirped and G0 can have a constant pitch and be planar.

In this way, manufacture of the gratings is simplified, for example through utilization of LIGA.

Furthermore, this completely new arrangement ensures for correct operation of the interferometric design, with the fringe pattern generated by the individual slits of the G0 grating lining up properly at the position of G2, which otherwise would not truly be satisfied.

It is to be noted that the gratings that are bent are each bent on a cylindrical surface having the required radius of curvature.

In an example, the grating that is not bent is a planar grating.

In an example, the adjacent pair of gratings that are bent are the first grating and the second grating.

In other words, the G0 and G1 gratings are bent, and the G2 grating can be planar.

In an example, the first grating and the second grating have the pitch attribute of having a varying grating pitch.

In other words, the G0 and G1 gratings are bent and chirped, and the G2 grating has a constant pitch.

In an example, the second grating and the third grating have the pitch attribute of having a varying grating pitch.

In other words, the G0 and G1 gratings are bent and the G1 and G2 gratings are chirped with G0 having a constant grating pitch.

In an example, the adjacent pair of gratings that are bent are the second grating and the third grating.

In other words, the G1 and G2 gratings are bent, and the G0 grating can be planar.

In an example, the first grating and the second grating have the pitch attribute of having a varying grating pitch.

In other words, the G1 and G2 gratings are bent and the G0 and G1 gratings are chirped and G2 has a constant grating pitch.

In an example, the second grating and the third grating have the pitch attribute of having a varying grating pitch.

In other words, the G1 and G2 gratings are bent and have varying grating pitches, and the G0 grating has a constant grating pitch.

In an example, the imaging data comprises dark field or phase contrast imaging data.

According to a second aspect, there is provided a system for X-ray imaging an object, comprising:

an apparatus for generating X-ray imaging data according to the first aspect;

a processing unit; and an output unit.

The processing unit is configured to control the apparatus, and is configured to control the output unit. The X-ray detector is configured to provide the processing unit with data relating to the detection of X-rays. The output unit is configured to output data representative of the object.

In an example, the system is a radiography or a CT system.

According to a third aspect, there is provided a method for generating X-ray imaging data, comprising:

a) positioning a first grating between an X-ray source and a second grating;

b) positioning the second grating between the first grating and a third grating;

c) positioning a third grating between the second grating and an X-ray detector;

d) positioning an object between the first grating and the third grating;

wherein, either the first or the third grating has a pitch attribute of having a constant grating pitch;

wherein, both gratings of an adjacent pair of gratings have a pitch attribute of having a varying grating pitch;

wherein, both gratings of an adjacent pair of gratings are bent such that a distance between the two adjacent gratings is constant as a function of fan angle; and e) detecting by the X-ray detector at least some of the X-rays transmitted by the three gratings and the object.

According to another aspect, there is provided a computer program element controlling apparatus as previously described which, if the computer program element is executed by a processing unit, is adapted to perform the method steps as previously described.

According to another aspect, there is provided a computer readable medium having stored computer element as previously described.

The computer program element, can for example be a software program but can also be a FPGA, a PLD or any other appropriate digital means.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
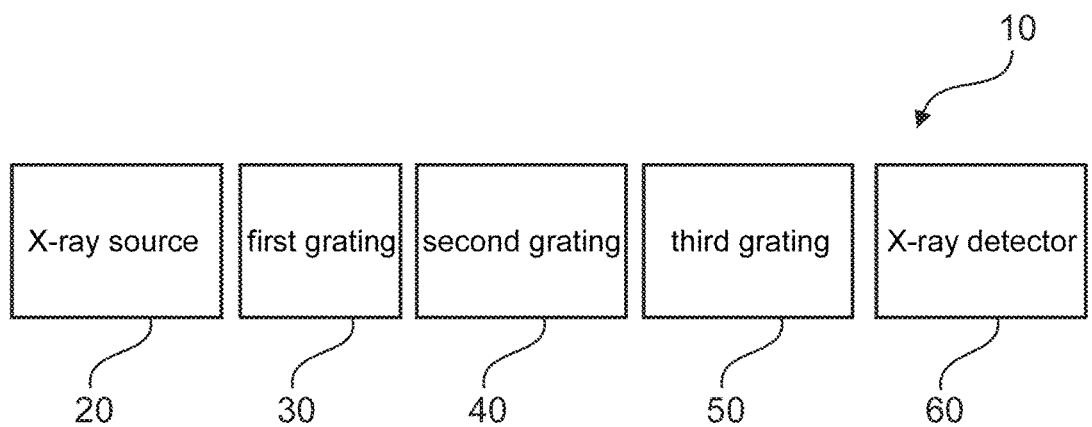
FIG. 1 shows a schematic set up of an example of an apparatus for generating X-ray imaging data.

FIG. 1 shows an example of an apparatus 10 for generating X-ray imaging data. The apparatus 10 comprises an X-ray source 20, a first grating 30, a second grating 40, a third grating 50, and an X-ray detector 60. The X-ray source 20 is configured to produce X-rays. The first grating 30 is positioned between the X-ray source 20 and the second grating 40. The second grating 40 is positioned between the first grating 30 and the third grating 50. The third grating 50 is positioned between the second grating 40 and the X-ray detector 60. At least part of the region between the first grating and the third grating forms an examination region for accommodating an object. Either the first grating or the third grating has a pitch attribute of having a constant grating pitch. Both gratings of an adjacent pair of gratings have a pitch attribute of having a varying grating pitch. Both gratings of an adjacent pair of gratings are bent such that a distance between the two adjacent gratings is constant as a function of fan angle. The X-ray detector is configured to detect at least some of the X-rays transmitted by the three gratings.

In an example, the radii of curvature of the gratings that are bent extends back to the position of the X-ray source.

Also, fan angle relates to an angle of the X-ray beam away from a centerline orientation.

According to an example, the grating that is not bent is a planar grating.

According to an example, the adjacent pair of gratings that are bent are the first grating and the second grating.

According to an example, the first grating and the second grating have the pitch attribute of having a varying grating pitch.

According to an example, the second grating and the third grating have the pitch attribute of having a varying grating pitch.

According to an example, the adjacent pair of gratings that are bent are the second grating and the third grating.

According to an example, the first grating and the second grating have the pitch attribute of having a varying grating pitch.

According to an example, the second grating and the third grating have the pitch attribute of having a varying grating pitch.

According to an example, the imaging data comprises dark-field and/or phase-contrast imaging data.

Figure 2:
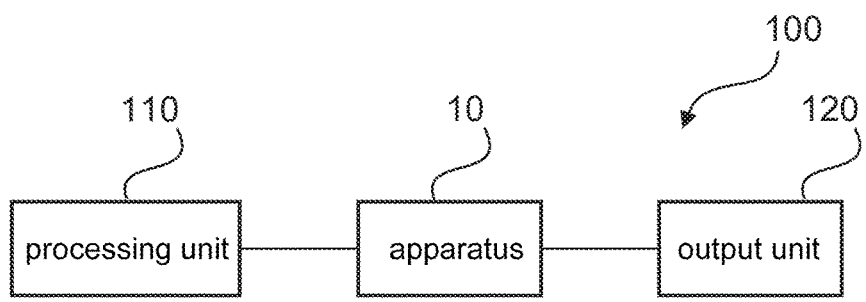
FIG. 2 shows a schematic set up of an example of a system for generating X-ray imaging data.

FIG. 2 shows an example of a system 100 for X-ray imaging an object. The system comprises an apparatus 10 for generating X-ray imaging data as described with respect to FIG. 1. The system 10 also comprises a processing unit 110, and an output unit 120. The processing unit 110 is configured to control the apparatus 10, and is configured to control the output unit 120. The X-ray detector 60 of the apparatus 10 is configured to provide the processing unit 110 with data relating to the detection of X-rays. The output unit 120 is configured to output data representative of the object.

According to an example, the apparatus is a radiography or CT apparatus.

According to an example, the system is a radiography or a CT system.

Figure 3:
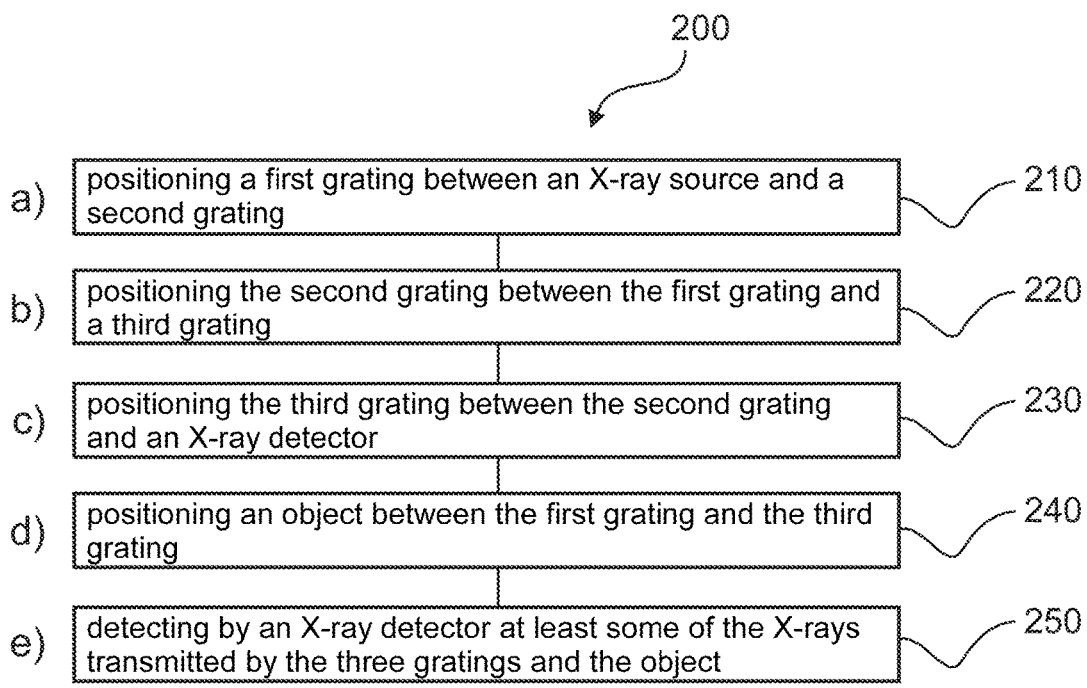
FIG. 3 shows a method for generating X-ray imaging data.

FIG. 3 shows a method 200 for generating X-ray imaging data in its basic steps. The method 200 comprises:

in a positioning step 210, also referred to as step a), positioning a first grating between an X-ray source and a second grating;

in a positioning step 220, also referred to as step b), positioning the second grating between the first grating and a third grating;

in a positioning step 230, also referred to as step c), positioning a third grating between the second grating and an X-ray detector;

in a positioning step 240, also referred to as step d), positioning an object between the first grating and the third grating;

wherein, either the first or the third grating has a pitch attribute of having a constant grating pitch;

wherein, both gratings of an adjacent pair of gratings have a pitch attribute of having a varying grating pitch;

wherein, both gratings of an adjacent pair of gratings are bent such that a distance between the two adjacent gratings is constant as a function of fan angle; and in a detecting step 250, also referred to as step e), detecting by an X-ray detector at least some of the X-rays transmitted by the three gratings and the object.

In an example, the grating that is not bent is a planar grating.

In an example, the adjacent pair of gratings that are bent are the first grating and the second grating.

In an example, the first grating and the second grating have the pitch attribute of having a varying grating pitch.

In an example, the second grating and the third grating have the pitch attribute of having a varying grating pitch.

In an example, the adjacent pair of gratings that are bent are the second grating and the third grating.

In an example, the first grating and the second grating have the pitch attribute of having a varying grating pitch.

In an example, the second grating and the third grating have the pitch attribute of having a varying grating pitch.

In an example, the imaging data comprises dark field or phase contrast imaging data.

The apparatus, system and method for generating X-ray imaging data are now described in more detail with reference to FIGS. 4-7.

Figure 4:
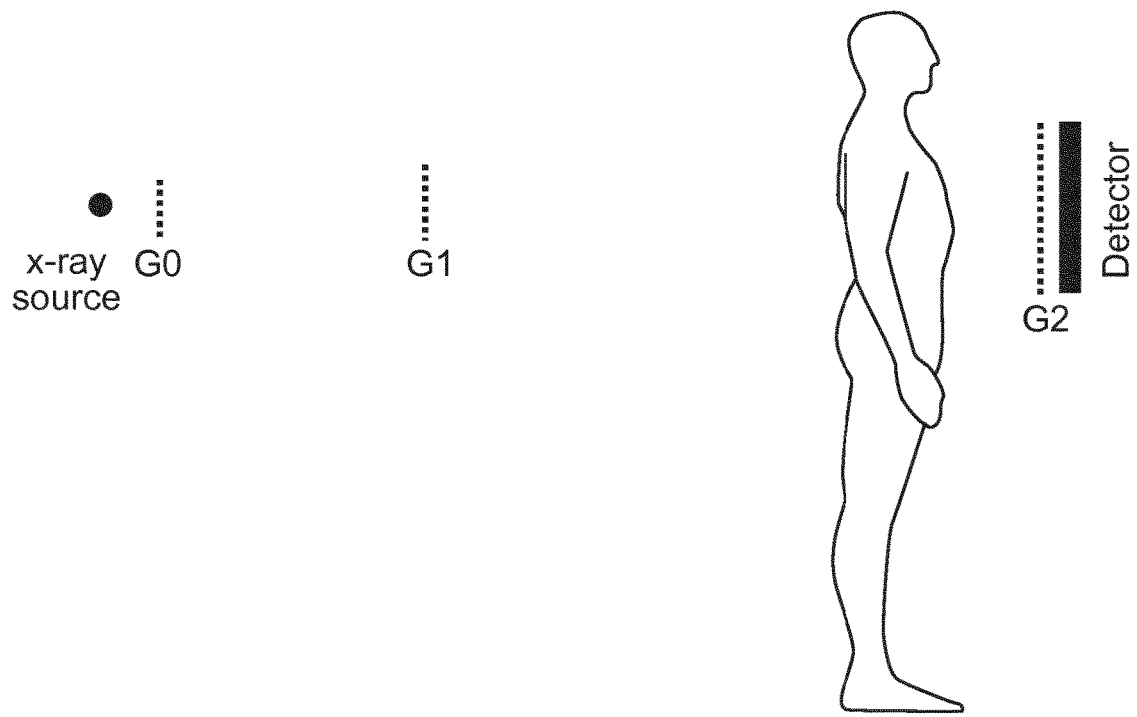
FIG. 4 shows a schematic illustration of a DAX/phase contrast system.

FIG. 4 shows a schematic illustration of a DAX apparatus with three gratings inserted into the optical path. Typically, G0 and G2 are absorber gratings and G1 is a phase grating. The object could however be situated between the G0 and G1 gratings.

Figure 5:
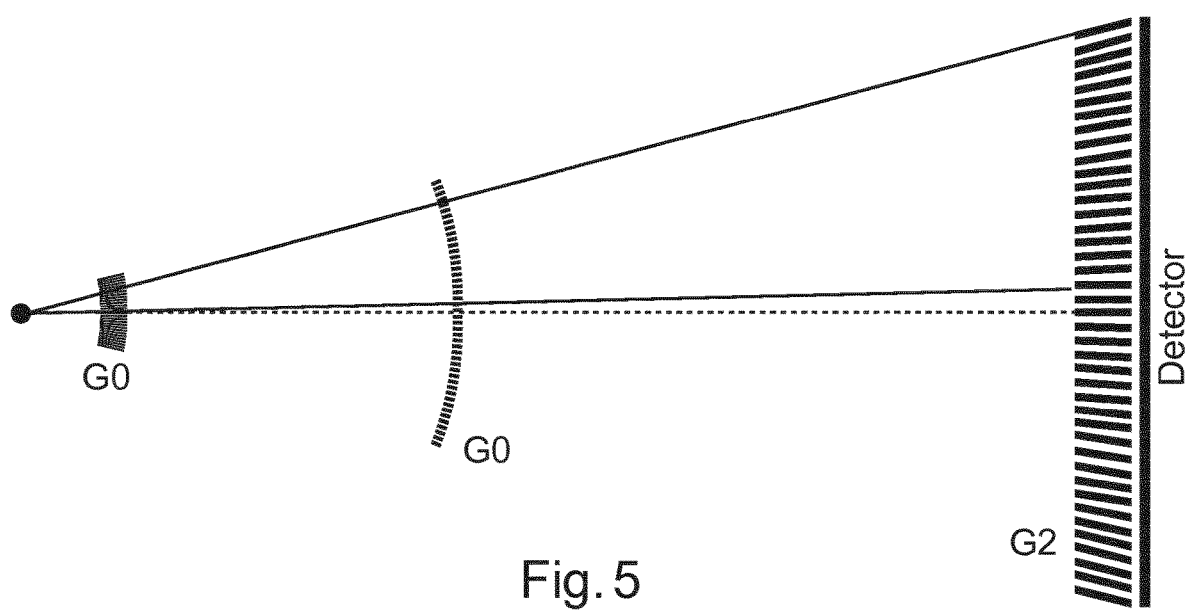
FIG. 5 shows a schematic illustration of an example of a grating arrangement with G0, G1 and G2 gratings.

FIG. 5 shows a grating arrangement, with G0 and G1 manufactured by LIGA (focused to the source by bending) and G2 manufactured by foil stacking (focused during manufacturing of a planar grating). The optical axis is indicated by the dashed line, with two exemplary rays at different fan angles shown as solid lines. Note that in this arrangement, the distance from G0 to G1 does not vary with the fan angle, but the distance from G1 to G2 does. This feature of such an arrangement is not however compliant with a standard Talbot-Lau interferometer design, until certain gratings are chirped as discussed in more detail below.

Figure 6:
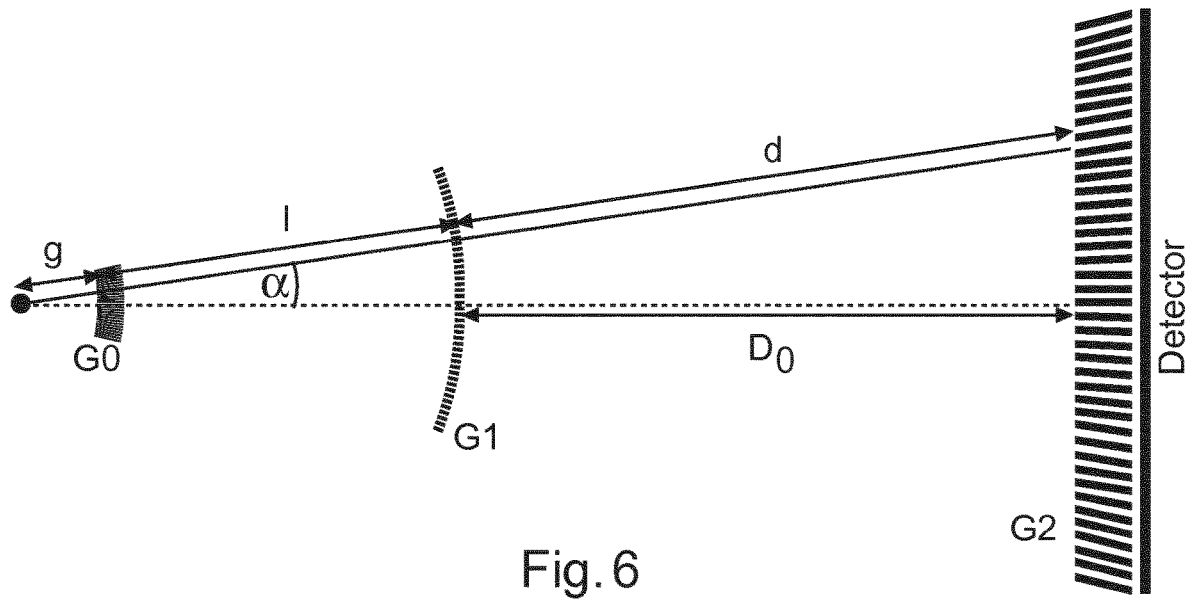
FIG. 6 shows a schematic illustration of an example of the grating arrangement used in the apparatus and system of FIGS. 1-2.

FIG. 6 shows exemplary rays at a fan angle $\alpha$. Regarding the design that addresses the issues described above, for the sake of simplicity, it is assumed that G1 is a $\pi/2$ phase grating or an absorbing grating. The concept can be easily adapted to a $\pi$ phase grating by accounting for the frequency doubling of the interference pattern at the location of G2. Now returning to the situation where G1 is a $\pi/2$ phase grating or an absorbing grating, the periods of the gratings G0, G1, and G2 can be denoted as $p_0$, $p_1$, and $p_2$ respectively, and the distance from G0 to G1 and G1 to G2 denoted as l and d, respectively. Then the following relationship must hold for proper operation of the system:

$$\frac{p_2}{p_0} = \frac{d}{l} \qquad \text{Equation (1)}$$

and $$p_2 = \frac{p_1(l+d)}{l} \qquad \text{Equation (2)}$$

Note that these relationships are required for proper operation since these relationships ensure that the fringe pattern generated by the individual slits of G0 line up properly at the position of G2. Note that there is usually another relationship related to the design energy of the system, namely $$d = \frac{p_1^2}{8\lambda} \qquad \text{Equation (3)}$$

where $\lambda$ is the wavelength of the systems design energy. As stated in the background section, it is state of the art to use gratings manufactured by LIGA and all gratings have a fixed period. These gratings are either all flat or all focused by bending. Note that Equations 1 and 2 hold in both scenarios. However, in the scenario illustrated in FIG. 6, according to the situation it does not hold. Consider a ray as illustrated in FIG. 6. Note that in this geometry, l and g, the distance from the focal spot to G0, are independent of $\alpha$ whereas d depends on $\alpha$ according to $$\cos \alpha (g + l + d) = g + l + D_0 \Rightarrow d = \frac{g + l + D_0}{\cos \alpha} - g - l$$

Then gratings G0 and G1 are fabricated with a chirped period. Given the formulae above, the period of G0 should be $$p_0(\alpha) = \frac{p_2 l}{d(\alpha)}$$

and the period of G1 should be $$p_1(\alpha) = \frac{p_2 l}{l + d(\alpha)}$$

Note that the grating structure, and therefore also the period of the gratings manufactured using LIGA, are produced in a lithographic step that easily allows to make such modulation of the period.

Returning to FIG. 6, rather than having G0 and G1 bent and chirped and G2 being planar and having a constant grating pitch, G0 and G1 can be bent and G2 can be planar and G0 can have a constant grating pitch, and G1 and G2 can be chirped.

Then, the above equations can be used to determine the required periods $p_1$ and $p_2$ as a function of fan angle $\alpha$.

Figure 7:
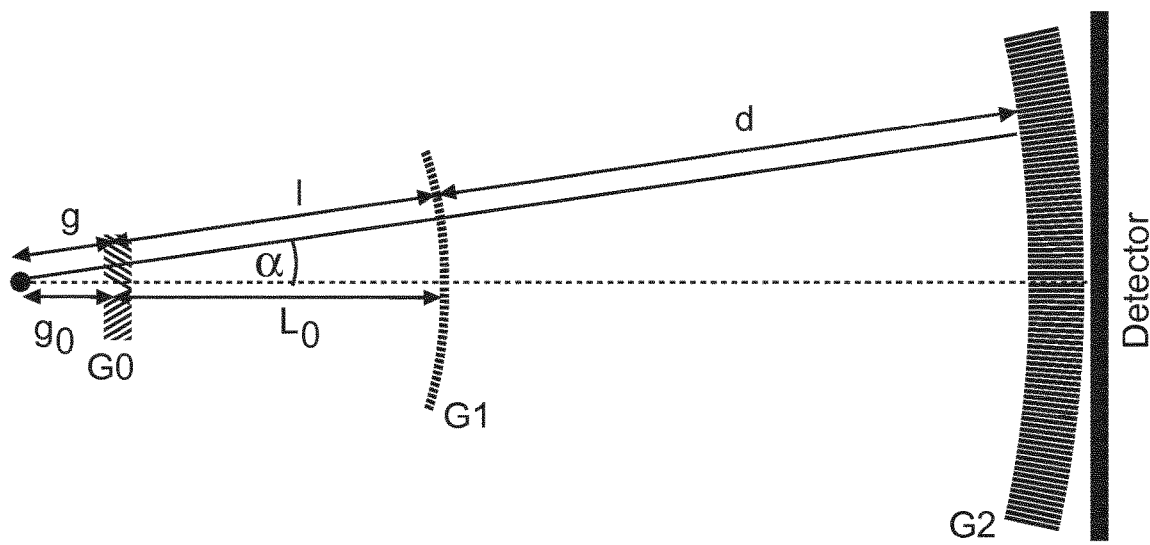
FIG. 7 shows a schematic illustration of an example of the grating arrangement used in the apparatus and system of FIGS. 1-2.

Furthermore, rather than having G0 and G1 bent and G2 planar, G0 can be planar and G1 and G2 bent, as shown in FIG. 7. Then, taking the case where G0 and G1 are chirped and G2 has a constant pitch, the following applies in order to calculate the necessary varying grating pitches:

$$g(\alpha) = \frac{g_0}{\cos \alpha} \quad l(\alpha) = g_0 + L_0 - g(\alpha) \quad d = const$$

$p_2$ should be constant $$p_0(\alpha) = \frac{p_2 l(\alpha)}{d} \quad \text{(see Eq. 1)}$$

$$p_1(\alpha) = \frac{p_2 l(\alpha)}{l(\alpha) + d} \quad \text{(see Eq. 2)}$$

However, again referring to FIG. 7, G0 can have a constant pitch, and G1 and G2 can be chirped. In which case the following applies to calculate the varying grating pitches:

$$g(\alpha) = \frac{g_0}{\cos \alpha} \quad l(\alpha) = g_0 + L_0 - g(\alpha) \quad d = const$$

$p_0$ should be constant $$p_2(\alpha) = \frac{p_0 d}{l(\alpha)} \quad \text{(see Eq. 1)}$$

$$p_1(\alpha) = \frac{p_2 l(\alpha)}{l(\alpha) + d} = \frac{p_0 d}{l(\alpha) + d} \quad \text{(see Eq. 2)}$$

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for generating X-ray imaging data, comprising:
   an X-ray source configured to generate X-rays;
   an X-ray detector configured to detect the X-rays;
   a first grating, a second grating, and a third grating respectively positioned between the X-ray source and the X-ray detector;
   wherein at least part of a region between the first grating and the third grating forms an examination region for accommodating an object;
   wherein (1) either the first grating or the third grating has a pitch attribute of a constant grating pitch, (2) each grating of an adjacent pair of the first, second and third gratings has a pitch attribute of a varying grating pitch, and (3) each grating of an adjacent pair of the first, second and third gratings is bent such that a distance between the two adjacent gratings is constant as a function of fan angle, such that fringe patterns generated by a plurality of slits of the first grating line up at a position of the third grating.

2. The apparatus according to claim 1, wherein the grating that is not bent is a planar grating.

3. The apparatus according to claim 1 wherein the adjacent pair of gratings that are bent is the first grating and the second grating.

4. The apparatus according to claim 1, wherein the first grating and the second grating have the pitch attribute of a varying grating pitch.

5. The apparatus according to claim 1, wherein the second grating and the third grating have the pitch attribute of a varying grating pitch.

6. The apparatus according to claim 1, wherein the adjacent pair of gratings that are bent is the second grating and the third grating.

7. The apparatus according to claim 6, wherein the first grating and the second grating have the pitch attribute of having a varying grating pitch.

8. The apparatus according to claim 6, wherein the second grating and the third grating have the pitch attribute of having a varying grating pitch.

9. The apparatus according to claim 1, wherein the imaging data comprises at least one of dark field imaging data and phase contrast imaging data.

10. A system for X-ray imaging an object, comprising:
    the apparatus according to claim 1; and
    an output unit configured to output data representative of the object.

11. The system according to claim 10, wherein the system includes a radiography or a CT system.

12. A method for generating X-ray imaging data, comprising:
    positioning a first grating, a second grating, and a third grating, wherein the first grating, the second grating, and the third grating are respectively positioned between an X-ray source and an X-ray detector; and
    positioning an object between the first grating and the third grating;
    wherein (1) either the first or the third grating has a pitch attribute of a constant grating pitch, (2) each grating of an adjacent pair of the first, second and third gratings has a pitch attribute of a varying grating pitch, and (3) each grating of an adjacent pair of the first, second and third gratings is bent such that a distance between the two adjacent gratings is constant as a function of fan angle, such that fringe patterns generated by a plurality of slits of the first grating line up at a position of the third grating; and
    detecting by the X-ray detector X-rays transmitted by the X-ray source.

13. A non-transitory computer-readable medium for storing executable instructions, which when executed by at least one processor, cause the at least one processor to perform a method for generating X-ray imaging data, the method comprising:
    positioning a first grating, a second grating, and a third grating, wherein the first grating, the second grating, and the third grating are respectively positioned between an X-ray source and an X-ray detector; and
    positioning an object between the first grating and the third grating;
    wherein (1) either the first or the third grating has a pitch attribute of a constant grating pitch, (2) each grating of an adjacent pair of the first, second and third gratings has a pitch attribute of a varying grating pitch, and (3) each grating of an adjacent pair of the first, second and third gratings is bent such that a distance between the two adjacent gratings is constant as a function of fan angle, such that fringe patterns generated by a plurality of slits of the first grating line up at a position of the third grating; and
    detecting by the X-ray detector X-rays transmitted by the X-ray source.

* * * * *